United States Patent [19]

Bhatia

[11] Patent Number: 4,835,293

[45] Date of Patent: May 30, 1989

[54] ATMOSPHERIC PRESSURE PROCESS FOR PREPARING PURE CYCLIC ESTERS

[75] Inventor: Kamlesh K. Bhatia, Newark, Del.

[73] Assignee: E. I. Du Pont De Nemours and Company, Wilmington, Del.

[21] Appl. No.: 17,418

[22] Filed: Feb. 24, 1987

[51] Int. Cl.[4] ............................................. C00Z 319/00
[52] U.S. Cl. .................................................. 549/274
[58] Field of Search .................................. 549/274, 518

[56] References Cited

U.S. PATENT DOCUMENTS

| | | | |
|---|---|---|---|
| 1,095,205 | 5/1914 | Gruter et al. | 549/274 |
| 2,163,109 | 6/1939 | Spangel | 260/338 |
| 2,163,268 | 6/1939 | Carothers et al. | 260/338 |
| 2,668,162 | 2/1954 | Lowe | 549/274 |
| 3,435,008 | 3/1969 | Schmitt et al. | 260/78.3 |
| 3,442,871 | 5/1969 | Schmitt et al. | 260/78.3 |
| 3,457,280 | 7/1969 | Schmitt et al. | 260/340.2 |
| 3,597,449 | 8/1971 | Deprospero et al. | 549/274 |
| 3,597,450 | 8/1971 | Schmitt et al. | 549/274 |
| 3,763,190 | 10/1973 | Ross et al. | 260/340.2 |
| 3,784,585 | 1/1974 | Schmitt et al. | 260/861 |
| 4,727,163 | 2/1988 | Bellis | 549/267 |

FOREIGN PATENT DOCUMENTS

| | | | |
|---|---|---|---|
| 47474 | 3/1982 | European Pat. Off. | 549/518 |
| 120581 | 9/1917 | Japan . | |
| 1108720 | 4/1968 | United Kingdom .. | |

OTHER PUBLICATIONS

Abstract of EP 47473 (03/82).

Primary Examiner—Glennon H. Hollrah
Assistant Examiner—Mark W. Russell
Attorney, Agent, or Firm—Craig H. Evans

[57] ABSTRACT

This invention relates to an improved process for preparing highly pure cyclic esters by heating a polymer of the corresponding α-hydroxy acid or its ester or a copolymer of α-hydroxy acid or its ester and a thermally stable polyether in the presence of an inert gas at atmospheric pressure. The cyclic ester is carried from the reaction with the inert gas to a solvent system.

19 Claims, 1 Drawing Sheet

F I G. 1
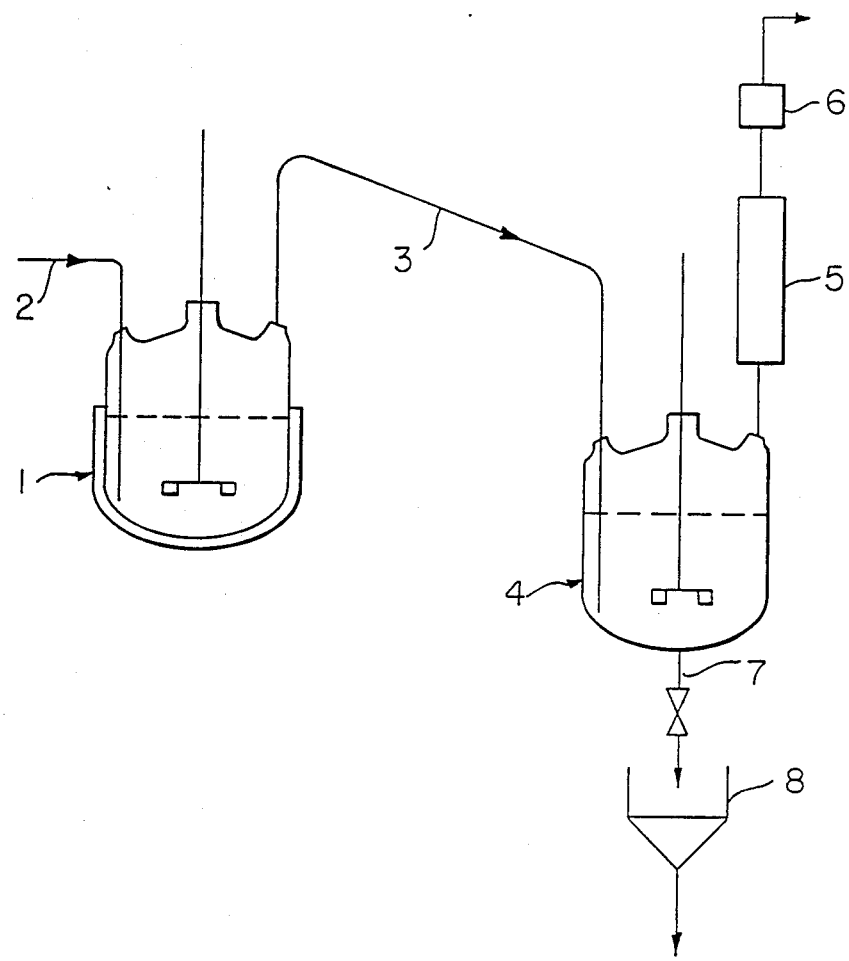

ATMOSPHERIC PRESSURE PROCESS FOR PREPARING PURE CYCLIC ESTERS

DESCRIPTION OF THE INVENTION

1. Technical Field

This invention relates to an improved process for preparing highly pure cyclic esters by cracking a polymer of the corresponding α-hydroxy acid or its ester or a block copolymer of the corresponding α-hydroxy acid or its ester and a thermally stable polyether in the presence of an inert gas at atmospheric pressure. The cyclic ester is carried from the reaction with the inert gas to a solvent system.

2. Background and Summary of the Invention

Cyclic esters of the general formula

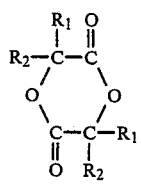

wherein $R_1$ and $R_2$ can be independently hydrogen or an aliphatic hydrocarbon having from 1 to about 6 carbon atoms, are a useful class of compounds that can be polymerized into high molecular weight polymeric plastic materials particularly useful in medical applications such as wound closure devices, orthopedic implants, and controlled release drug carriers. These applications require that the cyclic esters be highly pure so that they can be polymerized into long chain polymers.

In the past, these cyclic esters have been prepared by first condensing the corresponding α-hydroxy acid to a brittle polymeric form of the α-hydroxy acid. For example, if the desired product was glycolide, glycolic acid would be condensed to form a brittle polymer, polyglycolic acid. The polymeric material would then be ground to a fine powder and added slowly to a heated, evacuated vessel in which it would be depolymerized to a crude material which had to be subjected to an extensive and costly purification operation. This process suffered from excessive tar formation, low yields, and slow production rates. One attempt to improve upon that thermal cracking process and to prepare relatively pure glycolide is described in U.S. Pat. No. 3,763,190 to Donald L. Ross. That process required first making a salt of an O-haloacetylglycolic acid and then heating the salt to a sufficient temperature under vacuum to effect ring closure. Mineral salts had to be removed and the resulting glycolide separated and purified by sublimation.

A recent development claimed in U.S. Pat. No. 4,727,163, is a thermal cracking process that does not involve formation of a salt of a halogenated α-hydroxy acid. That process involves first making a block polymer comprising a thermally stable polyether core with α-hydroxy acid or its ester polymerized onto the core. Upon heating under vacuum conditions, the chain ends are thermally degraded to form a cyclic ester which can be condensed under vacuum. The condensed cyclic ester is a crude solid containing from about 1 to 12 weight percent acidic impurities. Other color-forming oily or waxy impurities are also present. This is particularly the case when starting with technical grade hydroxyacetic acid which contains other acidic impurities and evolves water when polymerized to make the starting polymer. Any residual water is believed to react with the cyclic ester to form the linear dimer of α-hydroxy acid. The crude glycolide must be reheated to remove it from the vessel that it condenses into. Impurities are then extracted in a suitable solvent and the cyclic ester is refined by one or more recrystallizations. Considerable yield loss occurs during the purification steps.

The process of the present invention is distinguished from these prior processes in that it can be run at atmospheric pressure or above. It comprises cracking a polymer of α-hydroxy acid or its ester or a block copolymer made from α-hydroxy acid or its ester and a thermally stable polyether (this polymer or block copolymer is also referred to as prepolymer) in intimate contact with an inert gas to form the cyclic ester. The cyclic ester vapors are carried from the cracking vessel by the inert gas and are brought into intimate contact with a solvent that preferentially removes impurities from the cyclic ester and the product is recovered in an easily handleable form that for most applications requires no further purification. The process may be run continuously or batchwise.

The process of the present invention offers numerous advantages over the processes of the prior art. It eliminates the need for high vacuum equipment and attendant plugging and safety problems. The process is safer to operate since the presence of inert gas eliminates the potential for explosive atmospheres that can result from air leaks in a vacuum process. Product removal is simplified since the cyclic ester forms into solid particles dispersed in the solvent. Remelting is not needed. Mechanical separation techniques such as filtration and centrifugation can be employed. Also, since the impurities dissolve in the solvent, the mechanically separated cyclic ester can for most applications be dried and used without the added purification steps of the prior art. The resulting product even without the solvent reslurrying and recrystallization steps of the prior art is a pure white, crystalline product having a low acid content. The process permits running the process of U.S. Pat. No. 4,727,163 with less expensive technical grade 70% hydroxyacetic acid to produce glycolide without purification by repeated recrystallizations. The process can also be used to produce pure cyclic esters without first forming the initial copolymer of U.S. Pat. No. 4,727,163. Higher yields can thus be obtained since product removal from the reactor is easier and the solids handling and solvent reslurrying steps of earlier processes are not needed. Also, as a result of high interfacial area in the reactor facilitated by the intimate contact with the inert gas, cracking time is not expected to increase as reactor size is increased. The process thus should be capable of being carried out on a larger scale then in the past. A continuous process is possible with this atmospheric pressure process.

DETAILED DESCRIPTION OF THE INVENTION

The process of this invention can use the block copolymer of U.S. Pat. No. 4,727,163 as its feed or it may use a polymer of the α-hydroxy acid. This block copolymer or polymer may be prepared from either the α-hydroxy acid or its ester. This block copolymer or polymer is alternatively referred to herein as prepolymer. The α-hydroxy acid is of the form $R_1R_2C(OH)$-

COOH, wherein $R_1$ and $R_2$ can be independently hydrogen or aliphatic hydrocarbon groups having from 1 to 6 carbons. The preferred α-hydroxy acids are glycolic acid and lactic acid. The ester of the α-hydroxy acid is of the form $R_1 R_2C(OH)COOR_3$, wherein $R_1$ and $R_2$ are defined as for the α-hydroxy acid and $R_3$ is an aliphatic hydrocarbon group having from 1 to 6 carbons. The preferred esters are methyl and ethyl glycolate and methyl and ethyl lactate. When the starting acid is glycolic acid or the starting ester is methyl or ethyl glycolate, the resulting cyclic ester is glycolide. When the starting acid is lactic acid or the starting ester is methyl or ethyl lactate, the resulting cyclic ester is lactide.

The reactor and scrubbing equipment employed can be chosen from any suitable gas-liquid-contacting device known in the art. For example, the reactor may be a sparged stirred tank, a bubble column, a spray reactor or a film reactor. A reactor such as a sparged stirred tank or a bubble column is preferred. Scrubbing equipment may be a sparged stirred tank, a spray column or a bubble column.

FIG. 1 depicts a typical reactor and scrubber arrangement for a batch process.

One skilled in the art can easily modify the batch process into a continuous process.

Referring to FIG. 1, the prepolymer is introduced to a well-mixed reactor (1) or is formed in the reactor and is heated to a sufficiently high temperature to crack the prepolymer. In FIG. 1, the assuring that the reactor contents are well mixed may be used. Cracking in the reactor is carried out at about atmospheric pressure or above. During this cracking, an inert gas, preferably nitrogen, is fed through line (2) which is positioned in the reactor so as to assure intimate contact with the prepolymer. Preferably the inert gas is preheated to the reaction temperature. The inert gas is injected below the surface of the material in the reactor. In FIG. 1, the point of addition is shown to be below the agitator. The flow rate of inert gas is set sufficiently high so as to not limit the rate of production. If the inert gas flow is too low, the yield may be adversely effected and the rate of production will be limited since the inert gas is needed to carry the cyclic ester vapors out of the reactor. Higher inert gas rates will not hinder the reaction but will require larger downstream equipment and will result in higher cost the inert gas flow rate should be 5 to 30 standard cubic feet per minute (scfm) per cubic foot of prepolymer and most preferably 10 to 20 scfm per cubic foot of prepolymer. The inert gas and the cyclic ester, vapors exit the reactor through heated line (3). The inert gas and the cyclic ester enter a well-mixed scrubber (4) below the solvent in the scrubber. The cyclic ester preferably enters the scrubber as a vapor but may be partially liquid. The scrubber in FIG. 1 is equipped with a condensor (5) and a dry ice trap (6) to condense any solvent that is vaporized when the hot cyclic ester and the inert gas are fed to the scrubber. The dry ice trap would be replaced by a suitably sized condensor in a larger scale facility. The scrubber is equipped with an agitator to assure good contact of the solvent with the incoming cyclic ester. Other means of assuring that the scrubber solution is well mixed may be used. Periodically or at the end of a production run the contents of the scrubber are discharged through line (7) to a filter (8) where the cyclic ester is collected as the filter cake and the solvent containing the impurities as the filtrate.

The scrubber (4) contains a solvent in which the impurities are preferentially soluble over the cyclic ester at the temperature of operation. The proper solvent can be determined by one skilled in the art based on knowledge of the solubilities of the impurities and the cyclic ester. Preferably, the solvent should be one in which impurities are highly soluble and the cyclic ester is significantly less soluble. Preferable solvents contain polar groups to dissolve the acid impurities. Preferably, the solvent would be chosen from the group comprising alcohols, ketones, ethers and esters and most preferably would be isopropyl alcohol. By operating the scrubber at a temperature lower than the freezing point of the cyclic ester, preferably at room temperature (20° to 45° C.), the cyclic ester will be solid particles dispersed in the solvent. As such, the cyclic ester product may be easily separated by mechanical means such as filtration or centrifugation and the solvent may be treated as waste, recycled to the scrubber or used in another process, depending on economic and environmental considerations.

When using a solvent in which the solubility of the cyclic ester is such that a significant amount of the cyclic ester is retained in the solvent with the impurities, the cyclic ester can be recovered by fractional crystallization.

Suitable temperatures for the cracking step range from about 215° to 290° C. with the preferred temperature range being from about 230° to 265° C. and the most preferred range being 240° to 255° C. There is theoretically no upper limit on the pressure at which the process is run. Practical considerations, however, make it preferable to keep the pressure to a minimum since higher pressures require a proportionately larger quantity of inert gas and result in a lower concentration of cyclic ester in the inert gas. Preferably, the pressure will be from about 0 pounds per square inch gauge (psig.) to about 10 psig. Most preferably, the pressure will be from about 0 psig. to about 5 psig. Operating at a slight vacuum would be within the equivalents envisioned so long as the pressure in the scrubber is above the saturation pressure of the solvent at the temperature of scrubber operation.

To run the process continuously, the reactor will be periodically or continuously purged to remove tars and fresh prepolymer will be added. The purge will either be treated as waste, recycled or used in another application depending on economic and environmental considerations. The solids collected in the solvent will be periodically or continuously discharged and the solvent will be replenished.

EXAMPLES

In order that the concept of the present invention may be more fully understood, the following examples are set forth. They are intended for illustration and not limitation.

Example 1

A prepolymer of hydroxyacetic acid (glycolic acid) on a thermally stable polyether core was prepared using the teachings of U.S. Pat. No. 4,727,163, using 70% technical grade hydroxyacetic acid. Three hundred ninety grams (390 gms) of 70% technical grade hydroxyacetic acid, 390 gms of Terethane 2000 ®, 7.4 gms of calcium oxide and 2 gms of antimony oxide ($SB_2O_3$) catalyst were placed in a nominal 1 liter stirred reactor (cylindrical reaction flask) equipped with a sparger positioned to permit the feeding of the nitrogen below the level of the agitator. The reactor was heated first at atmospheric pressure to remove most of the water and then at 10 mm mercury until no more water was seen condensing indicating that prepolymerization was complete. The temperature during this polymerization was raised to 195° C. and controlled at that temperature until the prepolymerization was complete.

After the prepolymerization was complete, a solvent scrubber equipped with an agitator and containing 600 cc of isopropyl alcohol was connected to the reactor as shown in FIG. 1. The temperature of the isopropyl alcohol at the beginning of the run was room temperature. No attempt to control temperature during the run was made. Dry nitrogen ($N_2$) flow to the reactor was started at a rate of about 0.35 standard cubic feet per minute (scfm) and the reactor temperature was increased gradually to about 255° C. A glass heat exchanger was used to prevent freezing of the glycolide in the line to the scrubber. The reactor temperature during the run ranged from about 250° to 260° C. The glycolide was recovered in the solvent scrubber as a slurry.

The reaction was stopped after 3.5 hours although glycolide was still coming over. Upon stopping the $N_2$ flow and the solvent scrubber stirrer, white crystalline glycolide particles quickly settled in the scrubber. The solvent layer, slightly discolored with yellowish impurities, was decanted off. The product was mixed with 200 cc of fresh isopropyl alcohol and discharged as a slurry to a filter. Nitrogen was blown over the filter cake to minimize atmospheric water contact. The filtration continued until no isopropyl alcohol droplets were observed coming out of the filtercake under vacuum conditions. The wet filter cake (containing from 10 to 15 weight % isopropyl alcohol) weighed 110 gms. The weight percent of acidic impurities (free acids as hydroxyacetic acid) in the filtered product were measured by dissolving 1 gram of the filtered product in 100 cc of a 1:1 mixture of methanol and acetone and titrating the solution with a standard sodium methoxide solution using an automatic titrator. The weight percent of acidic impurities was found to be 0.03%. A portion of the filter cake was dried by simply passing $N_2$ through it for 1½ hours at room temperature. Gas chromatographic analysis of a portion of the dried product dissolved in acetone showed about 0.06% isopropyl alcohol (IPA) in this dried product. The dried product was characterized by Differential Scanning Colorimetry (DSC) and Nuclear Magnetic Resonance Spectroscopy (NMR). The DSC showed a sharp melting curve with a peak at 85.3° C. and a melting point of 82.2° C., indicating high purity. The proton NMR would predict that, except for the residual IPA from drying, the product was more than 99.8% glycolide.

Example 2

The prepolymer in this example was prepared from methyl glycolate and a thermally stable polyether. One thousand grams (1000 gms.) methyl glycolate, 520 gms. of Terethane 2000 ®, 14.8 gms. calcium oxide and 4.9 gms. $Sb_2O_3$ catalyst were heated in a separate flask (not shown in FIG. 1) at atmospheric pressure to remove methanol. Methanol was removed by means of a fractionating column so as to retain the methyl glycolate in the reaction mass. The reaction temperature was maintained at 185° C. This polymerization reaction continued until no more methanol was observed coming out. The unreacted methyl glycolate was then removed by applying a vacuum at a temperature of 195° C. Calculations based on methanol recovered indicated that 47 weight % of the starting methyl glycolate was converted to the prepolymer.

The prepolymer was then transferred to a nominal 1 liter reactor where it was heated in intimate contact with $N_2$, as described in Example 1. Nitrogen flow was controlled at 0.35-0.4 scfm. Temperature was controlled at between 250°-265° C. The reaction was stopped after 4 hours. The starting isopropyl alcohol in the scrubber (as described in Example 1) was the filtrate from a prior experiment. Its starting temperature was room temperature and, as in Example 1, no attempt was made to control its temperature during the run. It was not decanted at the end of the run as in Example 1. The product slurry was filtered under a nitrogen blanket as in Example 1. The filter cake weighed 236 gms. The filtered product was pure white and crystalline. After several days of storage at room temperature, the product was washed with isopropyl alcohol to remove any surface moisture that might have been picked up during storage and was filtered. The filter cake was found to contain no detectable acidic impurities.

Examples 3 to 12

Examples 3 to 11 were run according to the procedure of Example 1, starting with 500 gms. of 70 weight % technical grade hydroxyacetic acid, 500 gms. Terethane 2000 ®, 9.5 gms. calcium oxide and 2.56 gms. antimony oxide in a nominal 1 liter stirred reactor. The nitrogen flow during the cracking step was about 0.35 scfm.

Example 12 was run according to the procedure of Example 1, starting with 5000 gms. of 70 weight % technical grade hydroxyacetic acid, 5000 gms. Terethane 2000 ®, 95 gms. calcium oxide and 25.6 gms. antimony oxide in a nominal 12 liter stirred reactor (spherical reaction flask). The agitator used in this example was the same agitator as used in the 1-liter examples. Thus, the inert gas contacting was not as effective as could have been obtained with a larger agitator. The isopropyl alcohol condensor was also the same as that used in the 1-liter experiments and could not handle the approximately 10 times greater gas rate that would be expected. Cracking had to be interrupted several times during the experiment due to the condensor being flooded. Nitrogen flow had to be limited to 2.5 to 3.0 scfm. With a suitably sized condensor, increased production rate would be expected.

The free acid content of the filter cake from each example, measured as in Example 1, was determined and is shown in Table 1. Also shown is the weight of filter cake and the cracking time of each experiment.

Example 13

Filter cake from each of Examples 3 to 12 was stored in capped glass bottles, which had been purged with dry nitrogen, in a refrigerator for up to several days. Part of the filter cake, wetted with isopropyl alcohol, from Experiment 3 (50 grams) and all the filter cake, wetted with isopropyl alcohol, from Experiments 4 through 12 were combined. The total weight of the combined filter cake after certain sampling losses was 1,995 gms. To facilitate mixing so as to assure a homogeneous composite slurry and to wash away any surface moisture picked up in storage and handling, an approximately equal weight of isopropyl alcohol was added and the resulting mixture was agitated. The resulting slurry was filtered in two batches to remove the isopropyl alcohol. The acidities of the filter cakes from these batches were 0.01 and 0.03 weight %. The filter cake was then dried in four batches each at 50° C. and 5 mm mercury in a rotary vacuum drier for 3 hours. The acidities of the dried batches were 0.03, 0.013, 0.02 and 0.016 weight %. The dried product contained no detectable isopropyl alcohol by gas chromatographic analysis. DSC analysis of the dried product showed a sharp melting curve with a peak at 83.2° C. and a melting point of 82.6° C. The purity of the glycolide was 99.92 mole %.

TABLE 1

| Exper. | Nominal Reactor Size (liters) | Filter Cake (grams) | Free Acid (weight %) | Cracking Time (hours) |
|---|---|---|---|---|
| 3 | 1 | 141 | 0.02 | 4 |
| 4 | 1 | 140 | 0.12, 0.03 | 3.5 |
| 5 | 1 | 145 | 0.063 | 3.25 |
| 6 | 1 | 135 | 0.065 | 3.5 |
| 7 | 1 | 142 | 0.035 | 3.25 |
| 8 | 1 | 141 | 0.061 | 3.25 |
| 9 | 1 | 135 | 0.037 | 3.5 |
| 10 | 1 | 147 | 0.039 | 3.25 |
| 11 | 1 | 165 | 0.044 | 3.5 |
| 12 | 12 | 825 | 0.039, 0.056 | 4 |

I claim:

1. An improved process for making a highly pure cyclic ester of the form

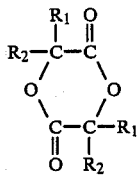

wherein $R_1$ and $R_2$ can be independently hydrogen or an aliphatic hydrocarbon having from 1 to about 6 carbon atoms by cracking a prepolymer comprising a polymer of an α-hydroxy acid or its ester or a block copolymer of an α-hydroxy acid or its ester on a thermally stable polyether wherein the improvement comprises cracking the prepolymer at a suitable temperature and at a pressure at or above atmospheric pressure while maintaining a sufficiently large flow of an inert gas, the inert gas being in intimate contact with the liquid prepolymer so as to create a large interfacial area between the prepolymer and the inert gas, to evolve the cyclic ester vapors.

2. The process of claim 1 comprising the further step of scrubbing the cyclic ester vapors and inert gas in a solvent.

3. The process of claim 1 wherein the temperature is from about 215° to 290° C. and the pressure from about 0 psig. to about 10 psig.

4. The process of claim 1 wherein the cyclic ester is glycolide or lactide.

5. The process of claim 3 wherein the temperature is from about 230° to 260° C. and the pressure is from about 0 psig. to about 5 psig.

6. The process of claim 4 wherein the temperature is from about 240° to 255° C. and the pressure is from about 0 psig. to about 10 psig.

7. The process of claim 1 wherein the inert gas flow is 5 to 30 scfm per cubic foot of prepolymer.

8. The process of claim 4 wherein the inert gas flow is 10 to 20 scfm per cubic foot of prepolymer.

9. The process of claim 7 wherein the inert gas is nitrogen.

10. The process of claim 8 wherein the inert gas is nitrogen.

11. The process of claim 2 comprising the additional step of separating the cyclic ester from the solvent.

12. The process of claim 2 wherein the solvent is a polar solvent in which the impurities are more soluble than the cyclic ester.

13. The process of claim 11 wherein the solvent is a polar solvent in which the impurities are more soluble than the cyclic ester.

14. The process of claim 12 wherein the cyclic ester is essentially insoluble in the solvent.

15. The process of claim 12 wherein the solvent is isopropyl alcohol.

16. The process of claim 13 wherein the temperature of the solvent is lower than the freezing point of the cyclic ester.

17. The process of claim 16 wherein the temperature of the solvent is between about 20° and 45° C.

18. The process of claim 17 wherein the cyclic ester is separated from the solvent by mechanical means.

19. The process of claim 18 wherein the mechanical means is filtration or centrifugation.

* * * * *